(12) United States Patent
Wilson et al.

(10) Patent No.: US 8,916,520 B2
(45) Date of Patent: Dec. 23, 2014

(54) MICROENCAPSULATED INSECTICIDE FORMULATIONS

(75) Inventors: Stephen L. Wilson, Indianapolis, IN (US); Raymond E. Boucher, Jr., Lebanon, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 85 days.

(21) Appl. No.: 12/714,922

(22) Filed: Mar. 1, 2010

(65) Prior Publication Data

US 2011/0052654 A1    Mar. 3, 2011

Related U.S. Application Data

(60) Provisional application No. 61/157,339, filed on Mar. 4, 2009.

(51) Int. Cl.
*A01N 37/18* (2006.01)
*A01N 25/28* (2006.01)

(52) U.S. Cl.
CPC ..................................... *A01N 25/28* (2013.01)
USPC ............................. 514/4.5; 514/359; 424/405

(58) Field of Classification Search
CPC ....... A01N 25/28; A01N 57/00; A01N 57/16; A01N 2300/00
See application file for complete search history.

(56) References Cited

U.S. PATENT DOCUMENTS

| | | | |
|---|---|---|---|
| 4,889,719 A | 12/1989 | Ohtsubo et al. | |
| 5,160,529 A | 11/1992 | Scher et al. | |
| 5,929,053 A | 7/1999 | Murakami et al. | |
| 6,440,443 B1 * | 8/2002 | Lee et al. | 424/408 |
| 2008/0038304 A1 * | 2/2008 | Nouvel | 424/409 |

FOREIGN PATENT DOCUMENTS

| | | |
|---|---|---|
| JP | 05-201814 | 8/1993 |
| RO | 91574 A2 | 4/1987 |
| RU | 2212797 | 9/2003 |
| WO | WO 92/13448 | 8/1992 |
| WO | WO-98/03065 A1 | 1/1998 |
| WO | WO-03/051116 A1 | 6/2003 |

OTHER PUBLICATIONS

International Searching Authority, International Search Report for PCT/US2010/025755, issued Jun. 14, 2010.
"Pyrinex CS—Material Safety Data Sheet," Feb. 28, 2000, pp. 1-10, XP55051463, Beer Sheva, Israel; Retrieved from the Internet: URL: http://www.masa.co.za/images/stories/pdf/msds/pyrinex250cs.pdf [retrieved on Jan. 28, 2013].
International Searching Authority, Written Opinion of the International Search Authority for PCT/US2010/025755, issued Apr. 9, 2011.
International Searching Authority, International Preliminary Report on Patentability PCT/US2010/025755, issued Jun. 9, 2011.

* cited by examiner

*Primary Examiner* — Lezah Roberts
*Assistant Examiner* — Nannette Holloman
(74) *Attorney, Agent, or Firm* — CW Arnett; Faegre Baker Daniels LLP

(57) ABSTRACT

Various microencapsulated insecticide formulations for the control of pests such as aphids and beet army worm. These formulations exhibit excellent knockdown activity towards both chewing and non-chewing pests as $LD_{50}$ values for toxicity in female rats in the range of about 2,500 mgKg$^{-1}$. Some of these formulations include a wall comprised of a polymer formed, for example, by an interfacial polycondensation of a water soluble monomer and a water insoluble monomer, which at least partially surround an organophosphate insecticide. In some aspects the organophosphate in the microcapsule is chlorpyrifos. The microcapsule have a diameter in the range of about 2 to about 25 micron and the wall has a thickness in the range of about 5 to about 25 nanometers.

19 Claims, 2 Drawing Sheets

CAPSULE BIOLOGY APHIGO

MICROENCAPSULATED INSECTICIDE FORMULATIONS

CROSS REFERENCE TO RELATED APPLICATIONS

This application claims the benefit of U.S. Provisional Patent Application Ser. No. 61/157,339, filed Mar. 4, 2009, which is expressly incorporated by reference herein.

FIELD OF THE INVENTION

Various aspects and embodiments relate generally to formulations of microencapsulated pesticides that exhibit advantageous biological, commercial and/or environmental properties.

BACKGROUND

Controlling insect populations is essential to modern agriculture, food storage and hygiene. Currently, encapsulated insecticidal formulations that are safe and effective play a significant role in controlling insect population. Properties of useful encapsulated insecticidal formulations include good efficacy against target pests, including good initial toxicity against targeted insects, ease of handling, stability, low toxicity towards 2,500 mgKg$^{-1}$ and advantageous resonance times in the environment. Some of these properties have been thought to be at odds with each other and designing useful insecticide formulations often involves creating formulations with characteristics that reflect a balance between these properties.

Given the great utility and importance of encapsulated insecticides there is a pressing and on-going need for new insecticide formulations that exhibit advantageous physical, chemical, biological and environmental properties. Various aspects and embodiment disclosed herein seek to address this need.

SUMMARY

One aspect is a pesticide formulation comprising an organophosphate pesticide and a polymer; wherein the polymer forms a capsule wall which at least partially encapsulates the organophosphate pesticide to form a microcapsule, the wall having an average thickness of between about 5 nm to about 25 nm, said microcapsule having an average diameter in the range of about 2 microns to about 6 microns. In one embodiment the microcapsule wall has an average thickness of between about 8 nm to about 12 nm, said microcapsule having an average diameter in the range of about 2 microns to about 6 microns.

In one embodiment the microcapsule includes at least one pesticide selected from the group of organophosphate pesticides selected from the group comprising: acephate, azinphos-mehyl, chlorfenvinphos, chlorethoxyfos, chlorpyriphos-methyl, diazinon, dimethoate, disulfoton, ethoprophos, fenitrothion, fenthion, fenamiphos, fosthiazate, malathion, methamidophos, methidathion, omethoate, oxydemeton-methyl, parathion, parathion-methyl, phorate, phosmet, profenofos, and trichlorfon. In still another embodiment the microcapsule includes the organophosphate pesticide chlorpyrifos. In yet another embodiment the microcapsule includes about at least between about 15 wt. percent to about 35 wt. percent chlorpyrifos.

In one embodiment the microcapsule is formed by an interfacial polycondensation between at least one oil soluble monomer selected, for example, from the group consisting of: diisocyanates, polyisocyanates, diacid chlorides, poly acid chlorides, sulfonyl chlorides, and chloroformates; and at least one water soluble monomer selected from the group consisting of, for example: diamines, polyamines, water soluble diols and water soluble polyols.

In one embodiment the microcapsule exhibits toxicity in female rats of greater than about 5,000 mgKg$^{-1}$ and an LC$_{50}$ value for the initial control of Cotton Aphids (APHIGO) of less than about 30 ppm chlorpyrifos. In still another embodiment the microcapsule exhibits toxicity in female rats of greater than about 2,500 mgKg$^{-1}$ and an LC$_{50}$ value for the initial control of Beet Army Worms (LAPHEG) of less than about 400 ppm chlorpyrifos.

Another aspect is a method of synthesizing a microcapsule with insecticidal properties, comprising the steps of providing an organophosphate insecticide, and at least one monomer; mixing the organophosphate insecticide, and at least one monomer; and forming a microcapsule, wherein the monomer forms a polymer, the polymer forming a wall, wherein the wall at least partially encompasses a portion of the insecticide, to form a microcapsule, the wall having an average thickness of between about 5 nm to about 25 nm, and the microcapsule having an average diameter in the range of about 2 microns to about 6 microns. In one embodiment the polymer comprising at least a portion of the microcapsule wall is formed by the interfacial polycondensation of at least one oil soluble monomer selected from the group including: diisocyanates, polyisocyanates, diacid chlorides, poly acid chlorides, sulfonyl chlorides, and chloroformates; and at least one water soluble monomer selected from the group including: diamines, polyamines, water soluble diols and water soluble polyols.

In one embodiment the microcapsule with insecticidal properties formed by a polymer that at least partially encompasses an organophosphate insecticide such as chlorpyrifos. The polymer forms a capsule wall that at least partially surrounds a portion of chlorpyrifos and the wall has an average thickness of between about 8 nm to about 12 nm, while the microcapsule has an average diameter in the range of about 2 microns to about 6 microns. In one embodiment the microcapsule includes on the order of at least 10 wt. percent chlorpyrifos. In yet another embodiment the polymer wall of the microcapsule at least partially surrounds at least one organophosphate pesticide is selected from the group that includes: acephate, azinphos-mehyl, chlorfenvinphos, chlorethoxyfos, chlorpyriphos-methyl, diazinon, dimethoate, disulfoton, ethoprophos, fenitrothion, fenthiom, fenamiphos, fosthiazate, malathion, methamidophos, methidathion, omethoate, oxydemeton-methyl, parathion, parathion-methyl, phorate, phosmet, profenofos, trichlorfon and the like.

Still another aspect is a method of controlling an insect population, comprising the steps of: providing an insecticidal particle formulation, wherein said particle includes: an organophosphate insecticide; and a polymer; wherein the polymer forms a capsule wall which at least partially encapsulates the organophosphate pesticide to form a microcapsule, in which the microcapsule wall has an average thickness of between about 5 nm to about 25 nm, and the microcapsule has an average diameter in the range of about 2 microns to about 6 microns; and applying said encapsulated insecticide to a surface, for example the leaves, stems or trunk of a plant.

One embodiment is a method for controlling an insect population that includes the steps of: forming a microcapsule with insecticidal properties the microcapsule includes a wall formed by the interfacial polycondensation of at least one oil soluble monomer selected from the group consisting of:

diisocyanates, polyisocyanates, diacid chlorides, poly acid chlorides, sulfonyl chlorides, and chloroformates; and at least one water soluble monomer selected from the group consisting of: diamines, polyamines, water soluble diols and water soluble polyols; and at least one organophosphate insecticide is selected from the group consisting of: acephate, azinphosmehyl, chlorfenvinphos, chlorethoxyfos, chlorpyriphos-methyl, diazinon, dimethoate, disulfoton, ethoprophos, fenitrothion, fenthiom, fenamiphos, fosthiazate, malathion, methamidophos, methidathion, omethoate, oxydemeton-methyl, parathion, parathion-methyl, phorate, phosmet, profenofos, and trichlorfon in which the polymeric wall component at least partially surrounds a portion of the insecticide to form a microcapsule. In one embodiment the microcapsule includes on the order of between about 15 wt. percent to about 35 wt. percent chlorpyrifos. In one embodiment the microcapsule used to control an insect population has a wall with an average thickness of between about 8 nm to about 12 nm, said microcapsule having an average diameter in the range of about 2 microns to about 6 microns.

In still another embodiment is a microencapsulated organophosphate insecticide used to control insect population with a toxicity value in female rats of greater than about 5,000 $mgKg^{-1}$ and an $LC_{50}$ for initial control of insects, such as cotton aphids, of less than about 30 ppm chlorpyrifos. In still another embodiment the microcapsule has a toxicity value in female rats of greater than about 2,500 $mgKg^{-1}$ and an $LC_{50}$ for initial control of insects, such as beet army worms, of less than 400 ppm chlorpyrifos.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention and together with the description, serve to explain the principles and operations of the invention.

DETAILED DESCRIPTION

Figure 1:
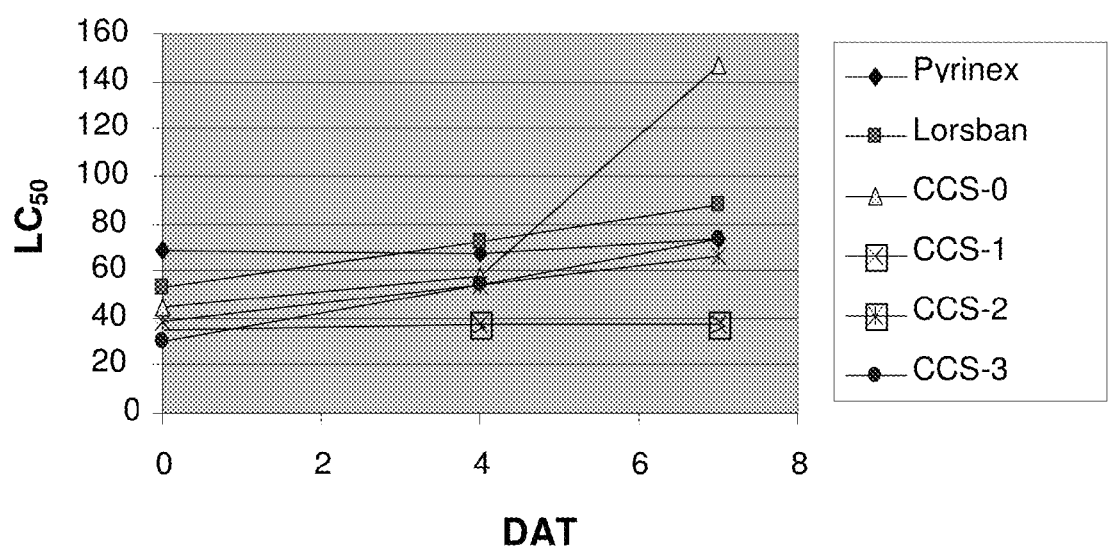
FIG. 1, $LC_{50}$ values (ppm of chlorpyrifos) plotted as a function of DAT, measured for various insecticide formulations, when tested for efficacy against Beet Army Worms (LAPHEG).
Figure 2:
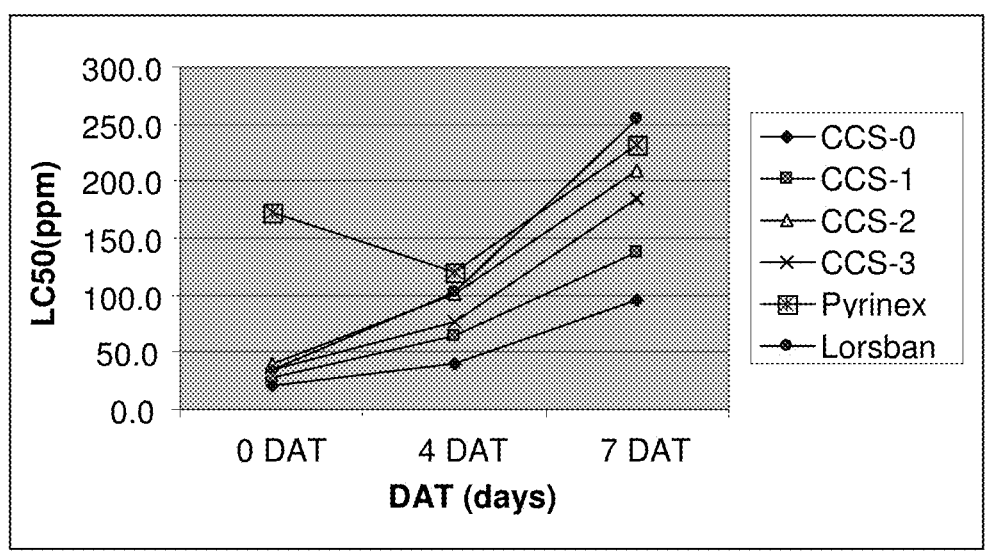
FIG. 2, $LC_{50}$ values (ppm of chlorpyrifos) plotted as a function of DAT, measured for various microcapsule and control formulations of chlorpyrifos tested for efficacy against Cotton Aphids (APHIGO).

For the purposes of promoting an understanding of the principles of the novel technology, reference will now be made to the preferred embodiments thereof, and specific language will be used to describe the same. It will nevertheless be understood that no limitation of the scope of the novel technology is thereby intended, such alterations, modifications, and further applications of the principles of the novel technology being contemplated as would normally occur to one skilled in the art to which the novel technology relates.

In one embodiment the invention provides a microencapsulated pesticide formulation that includes at least one pesticide for the extermination or control of at least one pest. In some formulations the pesticide is or at least includes at least one organophosphate pesticide. Organophosphate pesticides that can be used include, but are not limited to, the following compounds and various derivatives thereof: acephate, azinphos-mehyl, chlorfenvinphos, chlorethoxyfos, chlorpyriphos-methyl, diazinon, dimethoate, disulfoton, ethoprophos, fenitrothion, fenthiom, fenamiphos, fosthiazate, malathion, methamidophos, methidathion, omethoate, oxydemeton-methyl, parathion, parathion-methyl, phorate, phosmet, profenofos, and trichlorfon and the like.

The microcapsule shell can be formed by a polymer which wholly or partially covers a pesticide rich core. The shell of the microcapsule can be comprised by a wall, in which the wall is made up of a polymer. Some suitable polymers that can be used to construct the microcapsule wall includes at least one type of monomer linked together to form the polymer. In one embodiment the polymer wall is formed by the interfacial polycondensation of a monomer that is primarily water soluble and another monomer that is primarily insoluble in water. Suitable primarily water insoluble monomers that can be used to form the wall of the microcapsule include, but is not limited to, compounds such as diisocyanates, polyisocyanates, diacid chlorides, poly acid chlorides, sulfonyl chlorides, and chloroformates, and the like. Suitable primarily water soluble monomers that can be used to form the wall of the microcapsule include, but is not limited to, compounds such as diamines, polyamines, water soluble diols and water soluble polyols.

The wall comprising at least a portion of the shell of some microcapsules has an average thickness of between about 5 nm to about 25 nm the microcapsule may also have an average diameter in the range of about 2 microns to about 6 microns. In some embodiments the microcapsule wall has an average thickness of between about 8 nm to about 12 nm, said microcapsule having an average diameter in the range of about 2 microns to about 6 microns.

As used herein the term 'about' implies plus or minus ten percent of the stated value or range of values. For example: "about" 12, includes values ranging from 10.2 to 13.2; about 10 wt. percent encompasses formation that include between 9 to 11 wt. percent; and the like.

Microcapsules according to various aspects and embodiment exhibit good toxicity towards target insect populations and $LD_{50}$ values measured in female rats in the range of greater than about 2,500 $mgKg^{-1}$. In one set of embodiments the microcapsule has an $LD_{50}$ value measured in female rats in the range of greater than about 5,000 $mgKg^{-1}$, typically these values are expressed in terms of the amount of pesticide in the formulation as a fraction of the body weight of the test mammal. In still another embodiment, these microcapsules exhibit $LD_{50}$ values, measured in female rats, in the range of about 2,500 mg of active insecticide. The microcapsules are also effective at killing, inhibiting or repelling pests. Some embodiments are well suited to treat or control insect population on contact with the insect. For example, one formulation includes about 25 wt. percent chlorpyrifos and has an $LC_{50}$ value of about 30 pm of chlorpyrifos against Cotton Aphids (APHIGO) when a preparation of the microcapsule is applied to a population of insects or to an area adjacent to a population of insects.

In still another embodiment the microcapsule is useful for the treatment of chewing insects such as Beet Army Worms (LAPHEG). In one embodiment the formulation includes about 25 wt. percent chlorpyrifos, and has an $LC_{50}$ value of about 450 ppm for the initial control of Beet Army Worms of less than about 400 ppm chlorpyrifos when a preparation of the microcapsule is applied to an area of a plant adjacent to an insect population. In still another embodiment the formulation includes about 25 wt. percent chlorpyrifos and has an $LC_{50}$ value of about 50 ppm against Cotton Aphids (APHIGO) when a preparation of the microcapsule is applied to plants at a final level of less than about 30 ppm chlorpyrifos. In still another embodiment the microcapsule is useful for the treatment of chewing insects such as Beet Army Worms (LAPHEG). In one embodiment the formulation includes about 20 wt. percent chlorpyrifos, and is as effective as Lorsban® for the initial control of Beet Army Worms when applied at a rate of between 185-1,000 ppm chlorpyrifos. The same formulation is more effective than Lorsban® at controlling Beet Army Worms five days after its application.

Another aspect of the invention is a method of synthesizing a microcapsule with insecticidal properties. In one embodiment the method comprises the steps of providing an insecticide, for example, an organophosphate insecticide, and at least one molecule that can be used to form a coating which at least partially covers the insecticide forming at least a partial barrier between the insecticide and the environment. In one embodiment the coating, shell or at least components of the microcapsule wall is formed by a monomer which can be reacted with similar or different monomer to form a polymer that forms the wall of the microcapsule. Additional steps may include mixing the insecticide and the wall forming components together and reacting at least some of the components to form a wall structure that at least partially covers or coats or sequesters the insecticide within a portion of the microcapsule.

In one embodiment the insecticide provided to form the microcapsule is an organophosphate such as one of the following compounds: acephate, azinphos-mehyl, chlorfenvinphos, chlorethoxyfos, chlorpyriphos-methyl, diazinon, dimethoate, disulfoton, ethoprophos, fenitrothion, fenthiom, fenamiphos, fosthiazate, malathion, methamidophos, methidathion, omethoate, oxydemeton-methyl, parathion, parathion-methyl, phorate, phosmet, profenofos, trichlorfon and the like. In one embodiment the insecticide is chlorpyrifos.

In one embodiment the polymer comprising at least a portion of the microcapsule wall is formed by an interfacial polycondensation of at least one oil soluble monomer selected from the group including: diisocyanates, polyisocyanates, diacid chlorides, poly acid chlorides, sulfonyl chlorides, and chloroformates; and at least one water soluble monomer selected from the group including: diamines, polyamines, water soluble diols and water soluble polyols.

In one embodiment a microcapsule with insecticidal properties is formed by a polymer that at least partially encompasses an organophosphate insecticide such as chlorpyrifos. The polymer forms a wall that at least partially surrounds a portion of chlorpyrifos and the wall has an average thickness of between about 8 nm to about 12 nm. In another embodiment the wall has an average thickness of between about 5 nm to about 25 nm. In one embodiment the microcapsule has an average diameter in the range of about 2 microns to about 6 microns.

Still another aspect is a method of controlling an insect population, comprising the steps of: providing an insecticidal particle formulation, wherein said particle includes: an organophosphate insecticide; and a polymer; wherein the polymer forms a capsule wall which at least partially encapsulates the organophosphate pesticide to form a microcapsule, in which the microcapsule wall has an average thickness of between about 5 nm to about 25 nm, and the microcapsule has an average diameter in the range of about 2 microns to about 6 microns; and applying said encapsulated insecticide to a surface, for example the leaves, stems or trunk of a plant.

One embodiment is a method for controlling an insect population that includes the steps of: forming a microcapsule with insecticidal properties the microcapsule includes a wall formed by the interfacial polycondensation of at least one oil soluble monomer selected from the group consisting of: diisocyanates, polyisocyanates, diacid chlorides, poly acid chlorides, sulfonyl chlorides, and chloroformates; and at least one water soluble monomer selected from the group consisting of: diamines, polyamines, water soluble diols and water soluble polyols; and at least one organophosphate insecticide is selected from the group consisting of: acephate, azinphos-mehyl, chlorfenvinphos, chlorethoxyfos, chlorpyriphos-methyl, diazinon, dimethoate, disulfoton, ethoprophos, fenitrothion, fenthiom, fenamiphos, fosthiazate, malathion, methamidophos, methidathion, omethoate, oxydemeton-methyl, parathion, parathion-methyl, phorate, phosmet, profenofos, trichlorfon and the like in which the polymeric wall component at least partially surrounds a portion of the insecticide to form a microcapsule. In one embodiment the microcapsule includes on the order of about at least 10 wt. percent chlorpyrifos. In one embodiment the microcapsule used to control an insect population has a wall with an average thickness of between about 8 nm to about 12 nm, said microcapsule having an average diameter in the range of about 2 microns to about 6 microns.

In still another embodiment is a microencapsulated organophosphate insecticide used to control insect population that has a toxicity value in female rats of greater than about 5,000 $mgKg^{-1}$ and an $LC_{50}$ for initial control of insects, such as Cotton Aphids (APHIGO), of less than about 30 ppm chlorpyrifos. In still another embodiment the microcapsule has a toxicity value in female rats of greater than about 2,500 $mgKg^{-1}$ and an $LC_{50}$ for initial control of insects, such as Beet Army Worms (LAPHEG) of less than about 400 ppm chlorpyrifos.

One very successful approach taken by the pesticide producers to create insecticide formulations that exhibit a balance of advantageous properties has been to encapsulate insecticidal compounds with materials that exhibit low or no toxicity towards target insect population and/or that are more stable and/or easier to handle than the stand alone insecticide. These encapsulated formulations generally exhibit at least one desirable property relative to the non-encapsulated insecticide.

Particle formulations, including microcapsules that include at least one compound toxic to at least one insect species, especially an insect species that serves as a vector for human or animal disease or is a threat to commercially important plant species, are of great importance. Compounds that are toxic to insects include, but are not limited to, organophosphates such as acephate, azinphos-mehyl, chlorfenvinphos, chlorethoxyfos, chlorpyriphos, chlorpyriphos-methyl, diazinon, dimethoate, disulfoton, ethoprophos, fenitrothion, fenthion, fenamiphos, fosthiazate, malathion, methamidophos, methidathion, omethoate, oxydemeton-methyl, parathion, parathion-methyl, phorate, phosmet, profenofos, trichlorfon and the like.

Organochlorines are another class of molecules with insecticidal properties and include compounds such as, heptachlor, dichloro-diphenyl-trichloroethane, dicofol, endosulfan, chordane, mirex and pentachlorophenol. Another class of insecticides and insect repellants are the pyrethroids, these compounds are similar to the naturally occurring compound pyrethrum, and include, for example, alletherin, bifenthrin, cypermethrin, deltamethrin, permethrins, prallethrin, resmethrein, sumithrin, tetramethrin, tralomehtrin. transflurhrin and imiprothrin. Still another class of insecticides is similar to the naturally occurring compound nicotine, in addition to nicotine this class of insecticides and insect repellants includes the following compounds: acetamiprid, clothianidin, imidacloprid, nitenpyram, thiacloprid, and thiamethoxam.

Methods and compounds for forming particles that incorporate any method that can be used to form a shell, layer, coating or wall. Generally, the active ingredient in such particles is primarily located inside of the wall although full coverage of the active ingredient is not necessarily required to form a particle; particles include formulations in which at least a portion of the active ingredient is contiguous with the wall or even lies outside of at least a portion of the wall.

One method for forming a particle that includes forming a full or partial wall, which acts to separate either fully or partially an insecticide from the bulk solvent or environment is interfacial polycondensation of monomers. Briefly, a mixture of monomers is condensed to form a polymeric wall in the presence of at least one insecticide. A wall comprising a polymer essentially forms the outer boundary of the particle; the insecticide may be primarily concentrated within the particle bounded by a continuous or discontinuous wall that forms the outer contour of the particle. Monomers that can be used to form particles by the process of interfacial polycondensation may include primarily oil soluble monomers or set of such monomers and a water soluble monomer or set of such water soluble monomers. Oil soluble monomers include, for example, compounds selected from the group comprising: diisocyanates, polyisocyanates, diacid chlorides, poly acid chlorides, sulfonyl chlorides, chloroformates and the like. Water soluble monomers include, for example, compounds selected from the group comprising: diamines, polyamines, water soluble diols and polyols.

Various properties are required to form an insecticide or insect repellant with desirable characteristics. These properties include toxicity towards insects or at least the effect of repelling target insects or limiting their development and/or ability to reproduce. Still another desirable property is low or ideally absent toxicity towards other animals such as mammals, especially humans, or towards plants or non-target, especially, beneficial insect species.

Another desirable property is predictable and in most cases extended half-life of efficacy against target pests. Pesticide formulations that retain efficacy against target pest populations for extended periods of time may need to be applied less frequently or in lower initial amounts in order to control target pests thereby affording a savings in labor, energy and materials. Conversely, formulations that have long half-lives for example half-lives that extend significantly past the growing season of specific crops or peak infestation times of target pests may be considered an environmental nuisance under some circumstances.

Still another desirable property is predictable and in most cases extended residue times. Apply pesticide formulations that exhibit extended residue time can result in a cost savings as fewer applications are necessary over the course of a growing season or period of expected infestation. While it is possible to identify the ideal properties of an ideal insecticide because of differences in how they must be used, there is no ideal pesticide. The objective then is to create pesticide with specific properties that can be used as necessary under various unique conditions.

Disclosed herein, are microencapsulated pesticides in the form of particles possessing wall thicknesses and particle sizes that contribute to their utility under various conditions. Unexpectedly, these embodiments include insecticide formulations with particle sizes and wall thickness that result in particles that exhibit high initial knock-down activity including contact activity against target insects, toxicity $LD_{50}$ values against female rats on the order of about 2,500 $mgKg^{-1}$ and in some cases higher and favorable residue values.

Reference will now be made in detail to embodiment(s) of the invention, examples of which are illustrated in the accompanying drawings. Whenever possible, the same reference numerals will be used throughout the figures and tables to refer to the same or like compounds, compositions, devices and the like.

EXAMPLES

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

MATERIALS AND METHODS

Materials and Methods

Referring now to Table 1, a summary of the chemical and physical properties of some novel and some control formulations include chlorpyrifos and microcapsules. These capsules were produced by interfacial polycondensation as exemplified by a model procedure.

TABLE 1

| Capsule Formulations: | | | | |
|---|---|---|---|---|
| Lot Number | CCS-0 | CCS-1 | CCS-2 | CCS-3 |
| Target capsule diameter (□m) | 3 | 3 | 6 | 6 |
| Target capsule wall thickness (nm) | 5 | 10 | 5 | 10 |
| Chlorpyrifos (Wgt g) | 15.522 | 15.419 | 15.574 | 15.522 |
| Xylene ranged aromatic[1] | 9.313 | 9.251 | 9.344 | 9.313 |
| Polymethylene polyphenylisocyanate (g)[2] | 0.165 | 0.330 | 0.083 | 0.165 |
| Ethylenediamine (g)[3] | 0.040 | 0.079 | 0.020 | 0.040 |
| Poly (vinyl alcohol)GL03 PVA (g)[4] | 2.275 | 2.275 | 1.400 | 1.400 |
| Bentonite clay (g)[5] | 0.455 | 0.455 | 0.455 | 0.455 |
| Xathan gum(g)[6] | 0.057 | 0.057 | 0.057 | 0.057 |
| Polymeric surfactant (g)[7] | 1.266 | 1.266 | 0.779 | 0.779 |
| Water (g) | 32.570 | 32.926 | 33.266 | 33.445 |
| Measured capsule diameter (□m) | 3.3 | 3.5 | 6.2 | 5.9 |

Controls:
Lorsban 4E - NAF-163
Pyrinex ME - a commercial Chlorpyrifos Capsule Suspension marketed in Europe by Bayer.
[1]Aromatic 100 (g), Exxon Mobile Corp., Fairfax, VA.
[2]PAPI ® 27, Dow Plastics, Midland, MI
[3]Sigma-Aldrich
[4]Gohsenol GL03 (g), From Wippou Gohsei
[5]Veegam ®, R T Vanderbilt, Inc.
[6]Kelzan ® S, Kelco, Co.
[7]Atlox ® 4913, Croda

Preparation of Microcapsule Suspensions

Representative weights of the components used for capsule suspension preparation are summarized in the above Materials section. The preparation procedure was as follows: The indicated amount of PAPI 27 isocyanate monomer (Dow Chemical) was added to a 4 oz. wide-mouthed jar. An aromatic mixture including (62.5 wgt % chlorpyrifos) was added to the PAPI 27 to give 25 g of organic phase. This mixture was swirled until homogeneous. An aqueous phase was prepared comprised of the indicated amounts of poly(vinyl alcohol) (PVA, Gohsenol GL03, Nippon Gohsei), Veegum® (R. T. Vanderbilt), and Kelzan S® (Kelco) with sufficient DI water to give 35 g total aqueous phase. The aqueous phase was added to the organic phase to give a two-phase mixture. This mixture was emulsified using a Silverson L4RT-A high-speed mixer using the standard mixing assembly fitted with a ¾ in. mixing tube and general purpose emulsification head. Emulsification was achieved by first mixing at relatively low speed (~1000 rpm) with the tip of the mixing assembly located in the aqueous phase to draw in the organic phase until well emulsified. The speed was then increased in discrete increments. The mixer was stopped after each increase in speed and a size measurement taken. This process was continued until the desired particle size was obtained. A speed of ~4500-7500 rpm was typically required to reach the desired size. The crosslinking amine (ethylenediamine (EDA), Aldrich) was added dropwise as a 10% aqueous solution while stirring at a reduced speed that maintained good mixing. Following the completion of the amine addition the resulting capsule suspension was stirred for an additional minute, the indicated amount of Atlox 4913 (Uniqema) was added, and a final brief homogenization was performed to complete the preparation of the capsule suspension.

By carefully adjusting the length of time that the mixture was stirred and/or by adjusting the speed of the mixer, it is possible to produce encapsulated organophosphate insecticidal formulations of varying capsule size having a range of shell thicknesses.

Similarly, the amount of monomer, cross-linking agents, wetting agents, buffer, and the like can be adjusted to create microencapsulated organophosphate insecticidal formulations having varying capsule and shell thicknesses.

Measurement of Particle Size in Microcapsule Suspensions

Capsule suspension particle size distributions were determined using a Malvern Mastersizer 2000 light scattering particle sizer fitted with a small volume sample unit and using software version 5.12. Prior to measurement the samples were shaken or stirred well to insure homogeneity. The volume median distribution (VMD) is reported for each formulation in the Materials section above.

Calculation of Capsule Wall Thickness

The calculation of the amounts of capsule wall components needed to achieve a target wall thickness was based on the geometric formula relating the volume of a sphere to its radius. If a core-shell morphology is assumed, with the core comprised of the non wall-forming, water insoluble components (chlorpyrifos, solvent) and the shell made up of the polymerizable materials (oil and water soluble monomers), then equation (1) holds, relating the ratio of the volume of the core ($V_C$) and the volume of the core plus the volume of the shell ($V_S$) to their respective radii, where $r_S$ is radius of the capsule including the shell and $l_s$ is thickness of the shell.

$$\frac{V_c + V_s}{V_c} = \left(\frac{r_s}{r_s - l_s}\right)^3 \tag{1}$$

Solving equation (1) for the volume of the shell yields:

$$V_S = V_C\left(\left(\frac{r_S}{r_S - l_S}\right)^3 - 1\right) \tag{2}$$

Substituting masses ($m_i$) and densities ($d_i$) for their respective volumes ($m_S/d_S=V_S$ and $m_C/d_C=V_C$, where the subscript s or c refers to the shell or core, respectively) and solving for the mass of the shell gives:

$$m_S = m_C\frac{d_S}{d_C}\left(\left(\frac{r_S}{r_S - l_S}\right)^3 - 1\right) \tag{3}$$

It can be seen by comparing equations (2) and (3) that the effect of the density ratio $d_S/d_C$ is to apply a constant correction factor when masses are used to calculate the amounts of wall components needed to produce a capsule of desired size and wall thickness. When the density ratio remains constant for a series of capsules, as in the present study where the same core and shell materials were used for all of the preparations, elimination of the density ratio term only affects the absolute value of the wall thickness, not the relative differences. Since the relative differences are of primary importance, the approximation of eliminating the density ratio term was utilized to simplify the calculations, yielding equation (4)

$$m_S \approx m_C\left(\left(\frac{r_S}{r_S - l_S}\right)^3 - 1\right) \tag{4}$$

Making the substitutions $m_C=m_O-m_{OSM}$, $m_S=m_O+(f_{WSM/OSM})m_{OSM}-m_C$, and $f_{WSM/OSM}=m_{WSM}/m_{OSM}$ (the ratio of water soluble monomer to oil soluble monomer), where $m_O$ is the total mass of the oil components (Chlorpyrifos, solvent, oil-soluble monomer), $m_{OSM}$ is the mass of the oil-soluble monomer, and $m_{WSM}$ is the mass of the water-soluble monomer, and solving for $m_{OSM}$ yields:

$$m_{OSM} = \frac{m_O\left(\left(\frac{r_S}{r_S - l_S}\right)^3 - 1\right)}{f_{WSM/OSM} + \left(\frac{r_S}{r_S - l_S}\right)^3} \tag{5}$$

For the determination of $m_{OSM}$, the entire quantity of $m_{WSM}$ was used in the calculation as a convention. In the present study the water-soluble monomer was used on a 1:1 equivalent weight basis relative to the oil-soluble monomer for all of the capsule suspension preparations.

Biological Assays Used to Measure Activity Against Representative Species of Commonly Infested Posts Pyrinex CS® is a registered trademark of the Bayer Corporation. The compound is an encapsulated form of chlorpyrifos. The material used as a control in the experiment reported on herein was manufactured by Makhteshim Chemical Works, Be'er Sheva, Israel. According to a Material Safety Data Sheet provided by the supplier, Pyrinex CS has an oral toxicity, $LD_{50}$ value of >20,000 $mgKg^{-1}$.

Lorsban 4E is an emulsified concentrate of chlorpyrifos, marketed by Dow Agro Sciences, Indianapolis, Ind., USA. According to a Material Data Safety Sheet available through the supplier, Lorsban 4E has a $LD_{50}$ value in female rats of about 300 $mgKg^{-1}$.

Lorsban CS and Pyrinex were selected for use as controls in many of the tests because these formulations represent two extremes in chlorpyrifos formulations. Lorsban is an emulsified concentrate known for having excellent knock-down activity, and an $LD_{50}$ value of about 300 mgKg$^{-1}$ in female rats, while Pyrinex has an $LD_{50}$ value in female rats on the order of about 20,000 mgKg$^{-1}$ and poor knock-down activity. Toxicity data for Lorsban and Pyrinex are from the Material Safety Data Sheet of the two formulations.

Activity Against Beet Army Worms (LAPHEG):

Plants in 4-5 true leaf growth stage were sprayed with a track sprayer calibrated to deliver the equivalent of 200 L/Ha through a Teejet 8003 EVS nozzle at 40 psi. For time zero evaluations, plants were allowed to dry before leaf tissue was harvested. For residual tests, plants were aged in a greenhouse at 80-100° F. 70-80% relative humidity. 3×3 cm leaf discs were cut from sprayed plants and 1 leaf disc was placed in each well of a 32 well bioassay tray which had a thin layer of agar at the bottom. 5 second instar beet army worm larvae were placed in the center of each leaf disc and the tray was covered with a plastic lid. Larvae were held in an environmental chamber at 25 C/40% RH. Mortality was scored at 24 hours post infestation and a larva was considered dead if it could not move when prodded. Data were analyzed by using a log-dose probit transformation to determine the $LC_{50}$s and $LC_{50}$s and their 95% confidence level.

Activity Against Cotton Aphids (APHIGO).

Squash seedlings were invested with Cotton Aphids by placing small pieces of aphid-infested squash leaves from the laboratory colony (*Aphis Gossypii*) onto the squash cotyledon. Aphids were allowed to disperse on the leaves for 24 hours prior to treatment. Squash plants were sprayed with the test solution using a Devilbis hand held air brush sprayer. Plants were sprayed until runoff. Control was scored at 24 hours by randomly selecting one leaf from each plant and counting the number of live aphids present. Data were analyzed by using a log-dose probit transformation to determine the $LC_{50}$s and $LC_{90}$s values at their 95% confidence level. To determine residual control, uninfested squash plants were sprayed and allowed to age in a greenhouse at 80-90° F./70-80% RH. Plants were then infested as described above, and control was scored 24 hours later as noted.

Representative Methods Used to Measure Residue for Various Formulations Tested

Procedure: Formulations were diluted to provide 1 kg chlorpyrifos/200 L spray volume and sprayed on 12 plants at the 2-3 leaf stage (cotyledon). Plants were transported to the greenhouse (80-90° F./70-80% RH) and applied at a spray volume of 200 L/Ha at a rate of 1 kg a.i./Ha.

Sampling: Three cotyledons were removed from the set of treatments at 0, 3, 7, and 14 days after treatment. The leaves were weighed, placed in a 1 oz glass bottle to which 10 ml of acetonitrile was added. The bottles were capped and shaken for 45 minutes on a shaker table so that acetonitrile covered the entire leaf during shaking. A sample of acetonitrile was passed through a 0.45 micron PTFE syringe filter into an LC vial and submitted for assay.

Assay: GC/MS was used to measure the concentration of chlorpyrifos in the extract. No concentration of samples was required.

Methods Used to Measure Toxicology of Various Formulas in Female Rats Limit Test at 2,000 mgKg$^{-1}$ The objective of the study was to determine the potential of the test substance to produce lethal effects at a fixed dose level. An initial dose of 2,000 mgKg$^{-1}$ was administered to a single female animal. Since the initial animal survived following dosing, the test substance was administered sequentially to 4 additional females so a total of five animals were dosed.

Limit Test at 5,000 mgKg$^{-1}$

Three additional animals were dosed sequentially with 5000 mgKg$^{-1}$. Since the initial animal survived following dosing, the test substance was administered sequentially to two additional female rats. Since all animals survived, testing was terminated and the $LD_{50}$ values were considered greater than 5,000 mgKg$^{-1}$.

Test Species

Rats weighing 113.0-143.2 g at study start were used for this study. The rats were dosed starting at the age of about two months and they were necropsied between 2-3 weeks later.

Strain and Justification

Female F344/DuCrl rats were used in this study because of its general acceptance and suitability for acute oral toxicity testing, the availability of historical data, and the reliability of the commercial supplier. The test animals were obtained from Charles River Laboratories Inc. (Raleigh, N.C.). The age of the animals at the start of the study was 8-11 weeks Physical and Acclimation Each animal was evaluated by a laboratory veterinarian, or a trained animal/toxicology technician under the direct supervision of a laboratory veterinarian, to determine the general health status and acceptability for study purposes upon arrival at the laboratory (fully accredited by the Association for Assessment and Accreditation of Laboratory Animal Care International—AAALAC International).

Housing

The animals were housed two-three per cage in stainless steel cages, in rooms designed to maintain adequate conditions (temperature, humidity, and photocycle), and acclimated to the laboratory for at least one week prior to the start of the study. Animals were housed one per cage in stainless steel cages. The relative humidity was maintained within a range of 40-70%. The average room temperature was maintained at 22±1° C. (with a maximum permissible excursion of ±3° C.). A 12-hour light/dark photocycle was maintained for all animal room(s) with lights on at 6:00 a.m. and off at 6:00 p.m. Room air was exchanged approximately 12-15 times/hour. Cages had wire mesh floors and were suspended above absorbent paper. Cages contained a hanging feeder and a pressure activated lixit valve-type watering system.

Randomization and Identification

Rats were randomly assigned to dose groups using a computer program. Rats were identified via a code number transmitted by a subcutaneously implanted transponder (Bio-Medic Data Systems, Seaford, Del.).

Feed and Water

Animals were provided with LabDietâ Certified Rodent Diet #5002 (PMI Nutrition International, St. Louis, Mo.) in pellet form. Feed and municipal water was provided ad libitum. Analyses of the feed were performed by PMI Nutrition International to confirm the diet provides adequate nutrition and to quantify the levels of selected contaminants. Drinking water obtained from the municipal water source was periodically analyzed for chemical parameters and biological contaminants by the municipal water department. In addition, specific analyses for chemical contaminants were conducted at periodic intervals by an independent testing facility. There were no contaminants found in either the feed or water that would adversely impact the results or interpretation of this study.

Animal Welfare

In accordance with the U.S. Department of Agriculture animal welfare regulations, 9 CFR, Subchapter A, Parts 1-4, the animal care and use activities required for conduct of this study were reviewed and approved by the Institutional Animal Care and Use Committee (IACUC). The IACUC has determined that the proposed Activities were in full accordance with these Final Rules. The IACUC—approved Animal Care and Use Activities to be used for this study were Acute Tox 01, DCO 01, and Animal ID 01.

Dose Calculations

Individual doses were calculated based on the initial (fasted) body weights. All doses were administered volumetrically after correcting for specific gravity.

Dosing

Single animals were dosed in sequence. The time interval between dosing was determined by the onset, duration, and severity of toxic signs. Treatment of an animal at the next dose was delayed until reasonable confidence of survival of the previously dosed animal was achieved. Each animal was dosed by oral intubation using a stainless steel ball-tipped gavage needle attached to an appropriate syringe. The maximum volume administered at one time depended on the size of the animal. The volume did not exceed 10 ml/kg.

Daily Observations

This examination was typically performed with the animals in their cages and was designed to detect significant clinical abnormalities that were clearly visible upon a limited examination, and to monitor the general health of the animals. The animals were not hand-held for these observations unless deemed necessary. Significant abnormalities that could be observed include, but were not limited to: decreased/increased activity, repetitive behavior, vocalization, uncoordination/limping, injury, neuromuscular function (convulsion, fasciculation, tremor, twitches), altered respiration, blue/pale skin and mucous membranes, severe eye injury (rupture), alterations in fecal consistency, and fecal/urinary quantity. In addition, all animals were observed for morbidity, mortality, and the availability of feed and water at least twice daily.

Detailed Clinical Observations

A Detailed Clinical Observation (DCO) was conducted for all rats prior to test material administration for comparison with the observations recorded throughout the study. Animals were observed a minimum of two times on the day of treatment. A DCO was done each day (including weekends and holidays) during the study. Hand-held and open-field observations included a careful physical examination according to an established format. For scored DCOs only observations other than those that were typically expected were recorded. Observations were dictionary based, and the dictionary contained most of the common physical and neurologic abnormalities seen in toxicity studies. Since not all potential observations were contained in the dictionary, free-field descriptions also were allowed.

Pathology

Animals submitted alive for necropsy were anesthetized by the inhalation of carbon dioxide, the tracheas were exposed and clamped and the animals were euthanized by decapitation. A complete necropsy of all animals was conducted by a veterinary pathologist assisted by a team of trained individuals. The necropsy included an examination of the external tissues and all orifices. The eyes were examined in situ by application of a moistened glass slide to each cornea. The cranial cavity was opened and the brain, pituitary gland and adjacent cervical tissues examined. The skin was reflected from the carcass, the thoracic and abdominal cavities opened and the viscera examined. All tissues and the carcasses were discarded.

Statistics

Means and standard deviations of body weights were calculated. After each dose level was administered, the short-term and long-term outcome (results) were input into the OECD 425 AOT program. When the stopping criteria were engaged, the $LC_{50}$ and 95% confidence intervals were calculated.

Example 1

Results and Discussion

The cotton insecticide residue raw data for various control and experimental formulation are presented in Table 2. The data was analyzed in Minitab by assuming a first order degradation and fitting a line through a plot of log (average residue) versus time (days).

TABLE 2

Residue Data Collected from Tests of Novel Microcapsule and Control Formulations. Measurement were made initially and 6 and 13 Days after application.

| Formulation | A.I. Conc | Initial Leaf Weight | | | Initial CPF Analysis | | | Residue mg/kg | | | |
|---|---|---|---|---|---|---|---|---|---|---|---|
| | | 1 | 2 | 3 | 1 | 2 | 3 | 1 | 2 | 3 | Avg |
| Lorsban 4E | 44.1 wt % | 0.621 | 0.475 | 0.591 | 51 | 48 | 32 | 410.6 | 505.3 | 270.7 | 457.9 |
| Pyrinex CS | 250 g/L | 0.509 | 0.571 | 0.672 | 65 | 60 | 92 | 638.5 | 525.4 | 684.5 | 616.1 |
| CCS-0 | 20.1 wt % | 0.661 | 0.853 | 0.446 | 53 | 29 | 74 | 400.9 | 170.0 | 829.6 | 615.3 |
| CCS-1 | 19.9 wt % | 0.873 | 0.557 | 0.728 | 66 | 102 | 62 | 378.0 | 915.6 | 425.8 | 573.2 |
| CCS-2 | 20.4 wt % | 0.655 | 0.67 | 0.461 | 59 | 75 | 39 | 450.4 | 559.7 | 423.0 | 477.7 |
| CCS-3 | 20.3 wt % | 0.668 | 0.548 | 0.534 | 68 | 79 | 98 | 509.0 | 720.8 | 917.6 | 715.8 |

| Formulation | A.I. Conc | Leaf Weight | | | 6 Day Analysis | | | Residue mg/kg | | | |
|---|---|---|---|---|---|---|---|---|---|---|---|
| | | 1 | 2 | 3 | 1 | 2 | 3 | 1 | 2 | 3 | Avg |
| Lorsban 4E | 44.1 wt % | 0.999 | 1.008 | 1.259 | 1.1 | 1.4 | 1.2 | 11.0 | 13.9 | 9.5 | 11.5 |
| Pyrinex CS | 250 g/L | 1.303 | 1.207 | 1.244 | 22 | 30 | 34 | 168.8 | 248.6 | 273.3 | 230.2 |
| CCS-0 | 20.1 wt % | 1.351 | 1.121 | 1.157 | 0.6 | 0.7 | 1.3 | 4.4 | 6.2 | 11.2 | 7.3 |
| CCS-1 | 19.9 wt % | 1.108 | 1.051 | 1.356 | 6.8 | 6.1 | 5.9 | 61.4 | 58.0 | 43.5 | 54.3 |
| CCS-2 | 20.4 wt % | 1.186 | 1.096 | 1.496 | 1.5 | 2.6 | 2.3 | 12.6 | 23.7 | 15.4 | 17.2 |
| CCS-3 | 20.3 wt % | 1.419 | 1.183 | 1.007 | 2.1 | 3.8 | 3.7 | 14.8 | 32.1 | 36.7 | 27.9 |

TABLE 2-continued

Residue Data Collected from Tests of Novel Microcapsule and Control Formulations.
Measurement were made initially and 6 and 13 Days after application.

| Formulation | A.I. Conc | Leaf Weight 1 | 2 | 3 | 13 Day Analysis 1 | 2 | 3 | Residue mg/kg 1 | 2 | 3 | Avg |
|---|---|---|---|---|---|---|---|---|---|---|---|
| Lorsban 4E | 44.1 wt % | 1.45 | 1.021 | 1.027 | 0.7 | 0.5 | 1 | 4.8 | 4.9 | 9.7 | 6.5 |
| Pyrinex CS | 250 g/L | 1.09 | 1.261 | 1.245 | 11.9 | 16.8 | 26.8 | 109.2 | 133.2 | 215.3 | 152.6 |
| CCS-0 | 20.1 wt % | 1.029 | 1.264 | 1.334 | 0.8 | 1.2 | 1.2 | 7.8 | 9.5 | 9.0 | 8.8 |
| CCS-1 | 19.9 wt % | 1.603 | 1.09 | 1.296 | 1.5 | 1.1 | 1.1 | 9.4 | 10.1 | 8.5 | 9.3 |
| CCS-2 | 20.4 wt % | 1.343 | 1.297 | 1.305 | 1 | 0.6 | 0.8 | 7.4 | 4.6 | 6.1 | 6.1 |
| CCS-3 | 20.3 wt % | 1.168 | 1.41 | 1.13 | 0.8 | 0.9 | 0.7 | 6.8 | 6.4 | 6.2 | 6.5 |

The half life of chlorpyrifos in some was calculated from the slope of the fitted line (−0.693/slope); data collected for various control and experimental formulations which include chloropyrifo; shown in Table 3. The data are expressed in units of days.

TABLE 3

Half-Life of Chlopyrifos the Active Ingredient in Various Novel and Control Insecticidal Formulations

| Formulation | Half Life (Days) |
|---|---|
| Lorsban 4E | 2.2 |
| Pyrinex CS | 6.9 |
| CCS-0 | 2.2 |
| CCS-1 | 2.2 |
| CCS-2 | 2.1 |
| CCS-3 | 1.9 |

The plots for Lorsban 4E and CCS-0 are not as linear as the other plots. This may be because some of the chlorpyrifos volatilized or photolyzed between, by, or shortly after the day 6 measurement. For these reasons, it is possible that CCS-0 and Lorsban 4E have similar half lives which are shorter than indicated in this study and could be better estimated using the first two data points. While the half lives are useful in understanding the release profile of the capsule, the purpose of the study was to compare the residue levels of the encapsulated formulations. Each of the experimental formulations tested have residues values comparable to or lower than those of the control Lorsban 4E. Pyrinex is a very thick capsule; and it is very different from the experimental capsule formulations, and has a much longer half life and greater residues at 13 days. The experimental capsule formulations (CCS-0, CCS-1, CCS-2, CCS-3) produced higher residues than Lorsban 4E an emulsified concentrate of chlorpyrifos marketed by Dow, but significantly less than the Pyrinex CS a relatively thick walled capsule formulation marketed by Bayer.

Biology: Data from testing various formulations including some experimental formulations on Beet Army Worms (LAPHEG) are shown in Table 4.

TABLE 4

$LC_{50}$ and $LC_{90}$ Values (ppm) of Chlorpyrifos Determined by Measuring the Ability Various Novel Microcapsule and Control Formulations of Chlorpyrifos to Control Beet Army Worms (LAPHEG).

| Treatment | Rate | 0 DAT (# dead) | $LC_{50}$ ppm | $LC_{90}$ ppm | 4 DAT (# dead) | $LC_{50}$ pm | $LC_{90}$ ppm | 7 DAT (# dead) | $LC_{50}$ ppm | $LC_{90}$ ppm |
|---|---|---|---|---|---|---|---|---|---|---|
| L 4E | 1000 ppm | 40-40 | 529.43 | 828.1 | 31-40 | 716.02 | 1293.5 | 24-40 | 874.6 | 1813.7 |
|  | 500 ppm | 33-40 |  |  | 8-40 |  |  | 6-40 |  |  |
|  | 250 ppm | 3-40 |  |  | 1-40 |  |  | 1-40 |  |  |
|  | 125 ppm | 0-40 |  |  | 0-40 |  |  | 0-40 |  |  |
| CCS-0 | 1000 ppm | 40-40 | 441.46 | 667.46 | 34-40 | 572.1 | 1068.69 | 14-40 | 1469.26 | 6889.13 |
|  | 500 ppm | 25-40 |  |  | 17-40 |  |  | 10-40 |  |  |
|  | 250 ppm | 2-40 |  |  | 2-40 |  |  | 1-40 |  |  |
|  | 125 ppm | 5-40 |  |  | 0-40 |  |  | 1-40 |  |  |
| CCS-1 | 1000 ppm | 40-40 | 353.55 | 463.17 | 38-40 | 367.53 | 518.25 | 35-40 | 376.11 | 777.81 |
|  | 500 ppm | 38-40 |  |  | 35-40 |  |  | 31-40 |  |  |
|  | 250 ppm | 2-40 |  |  | 3-40 |  |  | 7-40 |  |  |
|  | 125 ppm | 3-40 |  |  | 1-40 |  |  | 2-40 |  |  |
| CCS-2 | 1000 ppm | 40-40 | 379.99 | 549.7 | 34-40 | 541.41 | 960.9 | 33-40 | 656.33 | 1002.08 |
|  | 500 ppm | 33-40 |  |  | 21-40 |  |  | 14-40 |  |  |
|  | 250 ppm | 3-40 |  |  | 1-40 |  |  | 0-40 |  |  |
|  | 125 ppm | 0-40 |  |  | 0-40 |  |  | 0-40 |  |  |
| CCS-3 | 1000 ppm | 40-40 | 299.58 | 450.59 | 35-40 | 542.41 | 1139.54 | 27-40 | 728.15 | 1526.94 |
|  | 500 ppm | 38-40 |  |  | 16-40 |  |  | 12-40 |  |  |
|  | 250 ppm | 11-40 |  |  | 4-40 |  |  | 2-40 |  |  |
|  | 125 ppm | 1-40 |  |  | 1-40 |  |  | 0-40 |  |  |
| Pyrinex | 1000 ppm | 36-40 | 681.66 | 1000.05 | 32-40 | 668.39 | 1286.75 | 28-40 | 730.82 | 1797.32 |
|  | 500 ppm | 6-40 |  |  | 10-40 |  |  | 10-40 |  |  |
|  | 250 ppm | 9-40 |  |  | 3-40 |  |  | 3-40 |  |  |
|  | 125 ppm | 1-40 |  |  | 0-40 |  |  | 1-40 |  |  |

Data from testing those formulations on Cotton Aphids is shown in Table 7.

TABLE 7

Data Collected by Measuring the Ability of Various Novel Microcapsule and Control Formulations of Chlopyrifos to Control Cotton Aphids (APHIGO). Experiments were replicated 4 times and the results are expressed as a percent (%) of the Control.

| Treatment | Rate | | Rep 1 | Rep 2 | Rep 3 | Rep 4 | % Control |
|---|---|---|---|---|---|---|---|
| Lorsban 4E 0 DAT | 400 | ppm | 0 | 0 | 0 | 0 | 0 |
| | 200 | ppm | 1 | 0 | 1 | 0 | 1 |
| | 100 | ppm | 8 | 5 | 4 | 11 | 7 |
| | 50 | ppm | 29 | 31 | 27 | 42 | 32 |
| | 25 | ppm | 56 | 70 | 66 | 44 | 59 |
| | 12.5 | ppm | 58 | 71 | 88 | 92 | 77 |
| Lorsban 4E 4 DAT | 400 | ppm | 15 | 12 | 17 | 45 | 22 |
| | 200 | ppm | 24 | 31 | 26 | 45 | 32 |
| | 100 | ppm | 56 | 59 | 52 | 65 | 58 |
| | 50 | ppm | 61 | 63 | 64 | 63 | 63 |
| | 25 | ppm | 72 | 68 | 77 | 63 | 70 |
| | 12.5 | ppm | 87 | 90 | 89 | 70 | 84 |
| Lorsban 4E 7 DAT | 400 | ppm | 56 | 67 | 64 | 59 | 62 |
| | 200 | ppm | 58 | 66 | 64 | 71 | 65 |
| | 100 | ppm | 78 | 54 | 70 | 75 | 69 |
| | 50 | ppm | 75 | 87 | 64 | 73 | 75 |
| | 25 | ppm | 75 | 81 | 85 | 80 | 80 |
| | 12.5 | ppm | 89 | 90 | 95 | 96 | 93 |
| Pyrinex 0 DAT | 400 | ppm | 18 | 12 | 14 | 8 | 13 |
| | 200 | ppm | 41 | 45 | 44 | 39 | 42 |
| | 100 | ppm | 61 | 76 | 55 | 59 | 63 |
| | 50 | ppm | 71 | 74 | 65 | 88 | 75 |
| | 25 | ppm | 91 | 87 | 81 | 94 | 88 |
| | 12.5 | ppm | 90 | 85 | 88 | 92 | 89 |
| Pyrinex 4 DAT | 400 | ppm | 42 | 53 | 44 | 41 | 45 |
| | 200 | ppm | 49 | 55 | 61 | 50 | 54 |
| | 100 | ppm | 59 | 71 | 65 | 52 | 62 |
| | 50 | ppm | 89 | 84 | 72 | 70 | 79 |
| | 25 | ppm | 83 | 88 | 81 | 71 | 81 |
| | 12.5 | ppm | 91 | 82 | 85 | 87 | 86 |
| Pyrinex 7 DAT | 400 | ppm | 35 | 29 | 31 | 24 | 30 |
| | 200 | ppm | 47 | 55 | 51 | 46 | 50 |
| | 100 | ppm | 63 | 58 | 57 | 71 | 62 |
| | 50 | ppm | 83 | 81 | 80 | 77 | 80 |
| | 25 | ppm | 81 | 90 | 92 | 86 | 87 |
| | 12.5 | ppm | 95 | 80 | 85 | 83 | 86 |
| CCS-0 0 DAT | 400 | ppm | 0 | 0 | 0 | 0 | 0 |
| | 200 | ppm | 0 | 0 | 0 | 0 | 0 |
| | 100 | ppm | 3 | 6 | 1 | 5 | 4 |
| | 50 | ppm | 29 | 36 | 20 | 19 | 26 |
| | 25 | ppm | 49 | 41 | 45 | 39 | 44 |
| | 12.5 | ppm | 51 | 43 | 56 | 65 | 54 |
| CCS-0 0 DAT | 400 | ppm | 6 | 1 | 3 | 7 | 4 |
| | 200 | ppm | 20 | 26 | 31 | 16 | 23 |
| | 100 | ppm | 32 | 39 | 49 | 42 | 41 |
| | 50 | ppm | 45 | 48 | 41 | 51 | 46 |
| | 25 | ppm | 42 | 54 | 58 | 61 | 54 |
| | 12.5 | ppm | 54 | 50 | 62 | 68 | 59 |
| CCS-0 7 DAT | 400 | ppm | 21 | 35 | 26 | 24 | 27 |
| | 200 | ppm | 33 | 41 | 35 | 29 | 35 |
| | 100 | ppm | 41 | 38 | 47 | 50 | 44 |
| | 50 | ppm | 52 | 55 | 58 | 61 | 57 |
| | 25 | ppm | 61 | 62 | 59 | 65 | 62 |
| | 12.5 | ppm | 68 | 71 | 65 | 72 | 69 |
| CCS-1 0 DAT | 400 | ppm | 0 | 0 | 0 | 0 | 0 |
| | 200 | ppm | 0 | 0 | 0 | 0 | 0 |
| | 100 | ppm | 7 | 1 | 4 | 1 | 3 |
| | 50 | ppm | 17 | 30 | 34 | 19 | 25 |
| | 25 | ppm | 51 | 58 | 49 | 63 | 55 |
| | 12.5 | ppm | 71 | 81 | 76 | 65 | 73 |
| CCS-1 4 DAT | 400 | ppm | 1 | 0 | 1 | 0 | 1 |
| | 200 | ppm | 14 | 24 | 26 | 19 | 21 |
| | 100 | ppm | 36 | 49 | 51 | 45 | 45 |
| | 50 | ppm | 47 | 56 | 63 | 66 | 58 |
| | 25 | ppm | 68 | 74 | 65 | 72 | 70 |
| | 12.5 | ppm | 87 | 77 | 61 | 74 | 75 |
| CCS-1 7 DAT | 400 | ppm | 25 | 30 | 21 | 28 | 26 |
| | 200 | ppm | 35 | 32 | 29 | 38 | 34 |
| | 100 | ppm | 55 | 49 | 51 | 53 | 52 |
| | 50 | ppm | 66 | 57 | 60 | 55 | 60 |
| | 25 | ppm | 78 | 83 | 81 | 88 | 83 |
| | 12.5 | ppm | 86 | 79 | 72 | 85 | 81 |
| CCS-2 0 DAT | 400 | ppm | 0 | 0 | 0 | 0 | 0 |
| | 200 | ppm | 0 | 0 | 0 | 0 | 0 |
| | 100 | ppm | 2 | 4 | 8 | 14 | 7 |
| | 50 | ppm | 56 | 33 | 31 | 44 | 41 |
| | 25 | ppm | 71 | 75 | 64 | 60 | 68 |
| | 12.5 | ppm | 80 | 84 | 77 | 86 | 82 |
| CCS-2 4 DAT | 400 | ppm | 5 | 3 | 4 | 12 | 6 |
| | 200 | ppm | 39 | 44 | 36 | 40 | 40 |
| | 100 | ppm | 51 | 48 | 57 | 52 | 52 |
| | 50 | ppm | 70 | 64 | 61 | 76 | 68 |
| | 25 | ppm | 73 | 85 | 66 | 79 | 76 |
| | 12.5 | ppm | 84 | 78 | 81 | 75 | 80 |
| CCS-2 7 DAT | 400 | ppm | 22 | 25 | 31 | 27 | 26 |
| | 200 | ppm | 46 | 51 | 55 | 58 | 53 |
| | 100 | ppm | 71 | 63 | 58 | 62 | 64 |
| | 50 | ppm | 75 | 71 | 67 | 70 | 71 |
| | 25 | ppm | 84 | 72 | 81 | 75 | 78 |
| | 12.5 | ppm | 91 | 87 | 83 | 89 | 88 |
| CCS-3 0 DAT | 400 | ppm | 0 | 0 | 0 | 0 | 0 |
| | 200 | ppm | 0 | 0 | 0 | 0 | 0 |
| | 100 | ppm | 0 | 1 | 5 | 2 | 2 |
| | 50 | ppm | 15 | 22 | 31 | 25 | 23 |
| | 25 | ppm | 76 | 71 | 59 | 33 | 60 |
| | 12.5 | ppm | 85 | 93 | 90 | 87 | 89 |
| CCS-3 4 DAT | 400 | ppm | 6 | 3 | 5 | 2 | 4 |
| | 200 | ppm | 31 | 36 | 27 | 12 | 27 |
| | 100 | ppm | 43 | 49 | 51 | 56 | 50 |
| | 50 | ppm | 54 | 61 | 55 | 64 | 59 |
| | 25 | ppm | 72 | 66 | 69 | 63 | 68 |
| | 12.5 | ppm | 84 | 86 | 75 | 89 | 84 |
| CCS-3 7 DAT | 400 | ppm | 31 | 20 | 24 | 27 | 26 |
| | 200 | ppm | 51 | 49 | 43 | 38 | 45 |
| | 100 | ppm | 61 | 58 | 74 | 69 | 66 |
| | 50 | ppm | 63 | 76 | 59 | 67 | 66 |
| | 25 | ppm | 77 | 75 | 69 | 71 | 73 |
| | 12.5 | ppm | 81 | 84 | 77 | 87 | 82 |

A summary of the $LC_{50}$ values measured for LAPHEG is shown below in Table 5. These data were collected initially and 4 and 7 days after exposure to the formulations.

TABLE 5

Summary of $LC_{50}$ Values (ppm) Determined by Measuring the Ability Various Novel Microcapsule and Control Formulations of Chlopyrifos to Control Beet Army Worms (LAPHEG). $LC_{50}$ Values for the Control of Beet Army Worms (LAPHEG)

| Formulations | 0 | 4 | 7 |
|---|---|---|---|
| Pyrinex ME | 681.66 | 668.39 | 730.82 |
| Lorsban 4E | 529.43 | 716.02 | 874.6 |
| CCS-0 | 441.46 | 572.1 | 1469.26 |
| CCS-1 | 353.55 | 367.53 | 376.11 |
| CCS-2 | 379.99 | 541.41 | 656.33 |
| CCS-3 | 299.58 | 542.41 | 728.15 |

These data are presented graphically in FIG. 1. Lorsban 4E is not as active at 0DAT as the experimental capsules and continues to decline over time. Pyrinex remains virtually unchanged with time and shows even less initial activity than Lorsban 4E. The values for Microcapsule formulation CCS-0

(3 micron, 5 nm) breaks suddenly after 4DAT even though it shows better activity than Lorsban 4E at 0 and 4 DAT. These suggest data that encapsulated chlorpyrifos microcapsule formulations of CCS-1 and CCS-2 are more active than the emulsified concentrate control. The formulation CCS-1 (partial size 3 microns, wall thickness 10 nm), exhibit excellent initial activity against insects such as LAPHEG and that this activity is maintained throughout the full 7 days of the test. Formulations CCS-2 (partial 6 micron, 5 nm) and CCS-3 (6 micron, 10 nm) exhibit similar changes in activity over time as with the 3 micron capsules the best initial activity is found with the thicker walled micron capsules. These observations seem reasonable in so far as this test is evaluating the toxicity of chlorpyrifos to a chewing pest.

TABLE 6

Measure of Insecticidal Activity of Various Chlorpyrifos Formulations Tested on Pepper Plants Infested with Beet Army Worms (LAPHEG).

| Treatment # | Formulation | Rate/ppm of Chlorpyrifos | 0 Time % Control | 2 DAT % Control | 5 DAT % Control | 8 DAT % Control |
|---|---|---|---|---|---|---|
| 13 | Lorsban 4E | 1000 | 100 | 100 | 100 | 13 |
| 14 | Lorsban 4E | 500 | 100 | 100 | 29 | 0 |
| 15 | Lorsban 4E | 250 | 100 | 92 | 13 | 0 |
| 16 | Lorsban 4E | 125 | 100 | 75 | 0 | 0 |
| 17 | CCS-4 | 1000 | 100 | 100 | 100 | 100 |
| 18 | CCS-4 | 500 | 100 | 100 | 100 | 21 |
| 19 | CCS-4 | 250 | 100 | 100 | 75 | 0 |
| 20 | CCS-4 | 125 | 100 | 63 | 17 | 0 |
| 21 | Untreated | | 0 | 0 | 0 | 0 |

Any encapsulation of chlorpyrifos that delays its volatility should provide longer control as long as the capsule releases the active upon ingestion by the larvae. The greater initial activity of the experimental capsules suggests that there is a significant loss of chlorpyrifos in a Lorsban 4E spray during the period in which the plants are allowed to dry before sampling. At the same time the reduced activity of the Pyrinex formulation suggests that the chlorpyrifos in these capsules is not as bioavailable as the chlorpyrifos found in experimental capsule formulations.

Biological data measured against the non-chewing pest Cotton Aphids (APHIGO) are shown in Table 7. $LD_{50}$ values calculated from these data are shown in Table 8.

TABLE 8

Summary of $LC_{50}$ Values (ppm) Determined by Measuring the Ability Various Novel Microcapsule and Control Formulations of Chlopyrifos to Control Cotton Aphids (APHIGO).

| | Calculated $LC_{50}$ Values (ppm) | | |
|---|---|---|---|
| Formulation | 0 DAT | 4 DAT | 7 DAT |
| CCS-0 | 20.54 | 40.30 | 95.71 |
| CCS-1 | 28.65 | 65.06 | 138.16 |
| CCS-2 | 39.98 | 101.12 | 209.7 |
| CCS-3 | 34.51 | 76.61 | 185.64 |
| Pyrinex | 172.50 | 120.33 | 231.65 |
| L 4E | 34.93 | 103.77 | 255.27 |

These data was collected initially and 4 and 7 days after exposure to the formulations.

And FIG. 2 is a graph of these $LD_{50}$ values versus DAT. Aphids pose a significant challenge to most capsule formulations because contact and not ingestion of chlorpyrifos is the primary route of exposure for this pest to the insecticide. Initially in this study the aphids were sprayed directly with the formulation and we expected that the encapsulated formulations would not be as active as the emulsified concentrates. Unexpectedly, initially the experimental capsules performed equal to or better than the formulation of Lorsban 4E and with better residual control. The ranking of the formulations tested from best to worst was as follows: CCS-0>CCS-1>CCS-3>CCS-2=L4E. These three micron microcapsules (CCS0 and CCS1) were superior to 6 micron microcapsules and microcapsules with thinner walls were superior to capsules with thicker walls. Pyrinex performed poorly in the test as would be expected for a conventional capsule formulation. The surprising results are that microcapsule formulations CCS0, CCS1, CCS2, CCS3 exhibit excellent activity against a non-chewing pest such as Cotton Aphids.

As illustrated in Table 9, insecticidal activity of various chlorpyrifos formulations were tested on squash plants infested with cotton aphids (APHIGO). The values in the table appear as a percent of the control. As shown in the table, cotton aphid control with CCS-4 at both 400 and 100 ppm of chlorpyrifos was better at 7 days than that measured with the Lorsban 4E formulations.

TABLE 9

| Formulation | Rate/ppm of Chlorpyrifos | 0 Time % Control | 4 DAT % Control | 7 DAT % Control |
|---|---|---|---|---|
| Lorsban 4E | 400 | 99 | 81 | 41 |
| Lorsban 4E | 100 | 96 | 56 | 31 |
| Lorsban 4E | 25 | 83 | 30 | 39 |
| CCS-4 | 400 | 100 | 97 | 98 |
| CCS-4 | 100 | 98 | 72 | 77 |
| CCS-4 | 25 | 92 | 29 | 32 |
| Untreated | | 0 | 0 | 0 |

The toxicology of microcapsule formulations CCS-0 and CCS-1 were studied. The microcapsule formulation CCS-0 had an oral toxicology rate towards female rats on the order of about $GL_{50}$>2000 $mgKg^{-1}$; while the microcapsule formulation CCS-1 had an $LD_{50}$>5000 $mgKg^{-1}$ value towards female rats. This same microcapsule also exhibits good knockdown and residual activity against Cotton Aphids (Table 12). As well as excellent knockdown and residual activity against Beet Army worms (Table 3). A residue value as good as Lorsban 4E (Table 14).

TABLE 12

Summary of $LC_{50}$ Values (ppm Chlorpyrifos) Collected by Comparing Various Formulations of Chlorpyrifos Tested Against Cotton Aphids (APHIGO).

| Chlorpyrifos Formulation | 0 DAT | 4 DAT | 7 DAT |
|---|---|---|---|
| Lorsban 4E | 34.93 | 103.77 | 255.27 |
| CCS-1 | 28.65 | 65.06 | 138.16 |
| Pyrinex ME | 172.5 | 120.33 | 231.65 |

TABLE 13

Summary of $LC_{50}$ Values (ppm of Chlorpyrifos) Measured by Comparing Various Formulations of Chlorpyrifos Tested Against Beet Army Worm (LAPHEG).

| Chlorpyrifos Formulation | 0 DAT | 4 DAT | 7 DAT |
|---|---|---|---|
| Lorsban 4E | 529.43 | 716.02 | 874.6 |
| CCS-1 | 353.55 | 367.53 | 376.11 |
| Pyrinex ME | 681.66 | 668.39 | 730.82 |

TABLE 14

Table Summarizing the Half-Life of Residues Measured for Various Chlorpyrifos Formulations.

| Chlorpyrifos Formulation | Half-life (days) |
|---|---|
| Lorsban 4E | 2.2 |
| CCS-1 | 2.2 |
| Pyrinex ME | 6.9 |

Experiment 2

Results of Toxicology Studies

Mortality

All animals survived the 14-Day observation period. Mortality results obtained by testing the toxicity of CCS-1 in female rats are presented in Table 10.

TABLE 10

Acute Oral Toxicity Study In F344/DUCRL Rats (up-down procedure) The Novel Microcapsule CCS-1 Mortality

| Dose (mg/Kg) | #/Dose | #Dead | Approximate Observed Time of Death (Day) |
|---|---|---|---|
| 2000 | 5 | 0 | — |
| 5000 | 3 | 0 | — |

No deaths noted.

No deaths noted.
Clinical Observations

Individual animal detailed clinical observations and clinical observations were made for rats dosed with these formulations. One of the five rats dosed at 2000 $mgKg^{-1}$ had urine perineal soiling on test day 9. The remaining four animals had no clinical observations throughout the study. Two of the 3 animals dosed at 5000 $mgKg^{-1}$ had red periocular soiling and urine perineal soiling, which resolved by test day 4. The third animal had no clinical signs throughout the study.

Body Weights

Mean and individual body weights were collected. Relative to the initial body weights, two rats dosed at 5000 $mgKg^{-1}$ lost weight by test day 2, but gained weight for the remainder of the study. All other animals given 2000 or 5000 $mgKg^{-1}$ gained body weight throughout the study. There were no gross pathologic observations.

CONCLUSIONS FROM TOXICITY STUDY

Under the conditions of this study, the acute oral $LD_{50}$ value for CCS-1 in female Fischer 344 rats is on the order of greater than 5000 $mgKg^{-1}$. See Table 11. The microcapsule formulations of chlorpyrifos disclosed herein have a toxicity $LD_{50}$ value greater that about 2,500, towards female rats and high knock-down activity against two common plant pests. Without being bound by any theory or specific explanation, these results are consistent with microcapsules having advantageous size and wall thickness. Given the wide range of possible microcapsule sizes and wall thicknesses that can be made it is fortuitous that these compounds were made and that they exhibit these advantageous biological characteristics.

TABLE 11

Summary of Oral Toxicity Results Collected by Comparing Various Chlorpyrifos Formulations in Rats

| Chlorpyrifos Formulation | $LD_{50}$ (mg/kg) |
|---|---|
| Lorsban 4E | 300 |
| CCS-1 | >5000 |

While the novel technology has been illustrated and described in detail in the figures and foregoing description, the same is to be considered as illustrative and not restrictive in character, it being understood that only the preferred embodiments have been shown and described and that all changes and modifications that come within the spirit of the novel technology are desired to be protected. As well, while the novel technology was illustrated using specific examples, theoretical arguments, accounts, and illustrations, these illustrations and the accompanying discussion should by no means be interpreted as limiting the technology. All patents, patent applications, and references to texts, scientific treatises, publications, and the like referenced in this application are incorporated herein by reference in their entirety.

We claim:

1. A pesticide formulation, comprising:
an organophosphate pesticide; and
a polymer forming a capsule wall which at least partially encapsulates the organophosphate pesticide to form a microcapsule, the wall having an average thickness of between about 5 nm to about 10 nm, said microcapsule having an average diameter in the range of about 2 microns to about 3 microns; wherein the wall is formed by an interfacial polycondensation between at least one oil soluble monomer selected from the group consisting of: diisocyanates, polyisocyanates, diacid chlorides, poly acid chlorides, sulfonyl chlorides and chloroformates; and at least one water soluble monomer selected from the group consisting of: diamines, polyamines, water soluble diols and water soluble polyols.

2. The pesticide formulation according to claim 1, the capsule wall having an average thickness of about 10 nm.

3. The pesticide formulation according to claim 1, wherein the organophosphate pesticide is selected from the group consisting of: acephate, azinphos-mehyl, chlorfenvinphos, chlorethoxyfos, chlorpyriphos-methyl, diazinon, dimethoate, disulfoton, ethoprophos, fenitrothion, fenthion, fenamiphos, fosthiazate, malathion, methamidophos, methidathion, omethoate, oxydemeton-methyl, parathion, parathion-methyl, phorate, phosmet, profenofos, and trichlorfon.

4. The pesticide formulation according to claim 1, wherein the organophosphate pesticide is chlorpyrifos.

5. The pesticide formulation according to claim 4, wherein the microcapsule includes between about 15 wt. percent to about 35 wt. percent chlorpyrifos.

6. The pesticide formulation according to claim 1, wherein said microcapsule exhibits toxicity in female rats of greater than about 5,000 mgKg$^{-1}$ and an $LC_{50}$ for initial control of cotton aphids of less than about 30 ppm chlorpyrifos.

7. The pesticide formulation according to claim 1, wherein said microcapsule exhibits toxicity in female rats of greater than about 2,500 mgKg$^{-1}$ and an $LC_{50}$ for initial control of beet army worm of less than about 400 ppm chlorpyrifos.

8. A method of synthesizing microcapsule, comprising the steps of:
providing an organophosphate insecticide, and at least one monomer;
mixing the organophosphate insecticide, and the at least one monomer; and
forming a microcapsule, the monomers forming a polymer, the polymer forming a wall, wherein the wall at least partially encompasses a portion of the insecticide, forming said microcapsule, the wall having an average thickness of between about 5 nm to about 10 nm, said microcapsule having an average diameter in the range of about 2 microns to about 3 microns; wherein the polymer is formed by an interfacial polycondensation between at least one oil soluble monomer selected from the group consisting of: diisocyanates, polyisocyanates, diacid chlorides, poly acid chlorides, sulfonyl chlorides and chloroformates; and at least one water soluble monomer selected from the group consisting of: diamines, polyamines, water soluble diols and water soluble polyols.

9. The method of synthesizing an insecticidal particle formulation according to claim 8, wherein the organophosphate pesticide is selected from the group consisting of acephate, azinphos-mehyl, chlorfenvinphos, chlorethoxyfos, chlorpyriphos-methyl, diazinon, dimethoate, disulfoton, ethoprophos, fenitrothion, fenthion, fenamiphos, fosthiazate, malathion, methamidophos, methidathion, omethoate, oxydemeton-methyl, parathion, parathion-methyl, phorate, phosmet, profenofos, and trichlorfon.

10. The method of synthesizing an insecticidal particle formulation according to claim 8, wherein said organophosphate pesticide is chlorpyrifos.

11. The method according to claim 10, wherein said microcapsule includes between about 15 wt. percent to about 35 wt. percent chlorpyrifos.

12. A method of controlling an insect population, comprising the steps of:
providing a insecticidal microcapsule formulation, the microcapsule including:
an organophosphate insecticide; and
a polymer; the polymer forming a wall which at least partially encapsulates the organophosphate pesticide to form a microcapsule, the wall having an average thickness of between about 5 nm to about 10 nm, said microcapsule having an average diameter in the range of about 2 microns to about 3 microns; and
applying said encapsulated insecticide to an insect population or to an area adjacent to an insect population;
wherein the polymer forming said wall is formed by an interfacial polycondensation between at least one oil soluble monomer selected from the group consisting of: diisocyanates, polyisocyanates, diacid chlorides, poly acid chlorides, sulfonyl chlorides and chloroformates; and at least one water soluble monomer selected from the group consisting of: diamines, polyamines, water soluble diols and water soluble polyols.

13. The method of controlling an insect population according to claim 12, where
the organophosphate insecticide is selected from the group consisting of: acephate, azinphos-mehyl, chlorfenvinphos, chlorethoxyfos, chlorpyriphos-methyl, diazinon, dimethoate, disulfoton, ethoprophos, fenitrothion, fenthion, fenamiphos, fosthiazate, malathion, methamidophos, methidathion, omethoate, oxydemeton-methyl, parathion, parathion-methyl, phorate, phosmet, profenofos, and trichlorfon.

14. The method of controlling an insect population according to claim 12, wherein said organophosphate pesticide is chlorpyrifos.

15. The pesticidal formulation, according to claim 1, wherein the capsule wall comprises a polymer of polymethylene polyphenylisocyanate.

16. The pesticidal formulation according to claim 1, wherein the capsule wall has an average thickness of about 5 nm.

17. The pesticidal formulation according to claim 1, wherein the microcapsule has an average diameter in the range of about 3 microns.

18. The pesticidal formulation according to claim 1, wherein the microcapsule has an $LC_{50}$ for initial control of a non-chewing pest equal to or better than that of a similar rate of pesticide applied as an emulsion.

19. The pesticidal formulation according to claim 1, wherein the microcapsule has an $LD_{50}$ for initial control of a non-chewing pest of 2000 mg/kg or greater.

* * * * *